(12) United States Patent
Tatkov

(10) Patent No.: US 12,023,443 B2
(45) Date of Patent: *Jul. 2, 2024

(54) BREATHING ASSISTANCE SYSTEM

(71) Applicant: Fisher & Paykel Healthcare Limited, Auckland (NZ)

(72) Inventor: Stanislav Tatkov, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 257 days.

This patent is subject to a terminal disclaimer.

(21) Appl. No.: 16/528,159

(22) Filed: Jul. 31, 2019

(65) Prior Publication Data

US 2019/0351168 A1 Nov. 21, 2019

Related U.S. Application Data

(63) Continuation of application No. 13/518,494, filed as application No. PCT/NZ2010/000260 on Dec. 22, 2010, now Pat. No. 10,556,079.

(Continued)

(51) Int. Cl.
*A61M 16/06* (2006.01)
*A61M 16/00* (2006.01)
(Continued)

(52) U.S. Cl.
CPC ........ *A61M 16/06* (2013.01); *A61M 16/0006* (2014.02); *A61M 16/0069* (2014.02);
(Continued)

(58) Field of Classification Search
CPC .............. A61M 16/06; A61M 16/0683; A61M 16/0057; A61M 16/0816; A61M 16/0875;
(Continued)

(56) References Cited

U.S. PATENT DOCUMENTS 1,896,716 A 2/1933 McKesson
2,313,999 A * 3/1943 Kreiselman ........... A61M 16/06
128/206.26

(Continued)

FOREIGN PATENT DOCUMENTS

AU 2010335069 6/2011
CN 1905917 1/2007
(Continued)

OTHER PUBLICATIONS

AU Patent Examination Report 1 for Patent Application No. 2010335069 dated Apr. 30, 2015, 6 pages.

(Continued)

*Primary Examiner* — Tu A Vo
(74) *Attorney, Agent, or Firm* — Knobbe, Martens, Olson & Bear, LLP

(57) ABSTRACT

A user interface has a non-sealing nasal cannula and a mask arranged about the nasal cannula, the mask including a seal configured with a user's face to allow the interface to be pressurised, the cannula configured to deliver breathing gases to the nares of a user at a flow rate exceeding the intended user's peak inspiratory flow requirements so that the mask and the user's pharynx are flushed continuously with fresh breathing gases to reduce dead space.

17 Claims, 10 Drawing Sheets

Related U.S. Application Data

(60) Provisional application No. 61/289,544, filed on Dec. 23, 2009.

(51) Int. Cl.
*A61M 16/08* (2006.01)
*A61M 16/10* (2006.01)
*A61M 16/16* (2006.01)

(52) U.S. Cl.
CPC .... *A61M 16/0616* (2014.02); *A61M 16/0622* (2014.02); *A61M 16/0633* (2014.02); *A61M 16/0666* (2013.01); *A61M 16/109* (2014.02); *A61M 16/1095* (2014.02); *A61M 16/0683* (2013.01); *A61M 16/0816* (2013.01); *A61M 16/16* (2013.01); *A61M 16/161* (2014.02); *A61M 2205/3365* (2013.01); *A61M 2205/3368* (2013.01)

(58) Field of Classification Search
CPC .......... A61M 16/0622; A61M 16/0616; A61M 16/109; A61M 16/0069; A61M 16/1095; A61M 16/0666; A61M 2205/3368; A61M 16/16; A61M 2205/3365
See application file for complete search history.

(56) References Cited

U.S. PATENT DOCUMENTS

| | | | |
|---|---|---|---|
| 2,375,803 A | | 5/1945 | Chase et al. |
| 2,663,297 A | | 12/1953 | Turnberg |
| 2,675,803 A | | 4/1954 | Kaslow |
| 2,693,800 A | | 11/1954 | Caldwell |
| 2,868,199 A | | 1/1959 | Hudson |
| 3,330,274 A | * | 7/1967 | Bennett ................. A61M 16/06 128/206.26 |
| 3,441,020 A | * | 4/1969 | Wortz ............... A61M 16/0683 128/205.25 |
| 3,513,844 A | | 5/1970 | Smith |
| 4,201,205 A | | 5/1980 | Bartholomew |
| 4,231,363 A | | 11/1980 | Grimes |
| 4,248,218 A | * | 2/1981 | Fischer ............... A61M 16/009 128/204.18 |
| 4,328,767 A | | 5/1982 | Peterson |
| 4,328,797 A | | 5/1982 | Rollins, III et al. |
| 4,354,488 A | | 10/1982 | Bartos |
| 4,944,310 A | | 7/1990 | Sullivan |
| 5,005,571 A | * | 4/1991 | Dietz .................... A61M 16/06 128/205.25 |
| 5,400,781 A | | 3/1995 | Davenport |
| 5,474,060 A | | 12/1995 | Evans |
| 6,357,437 B1 | | 3/2002 | Jacques |
| 6,397,841 B1 | * | 6/2002 | Kenyon ................. A61M 16/08 128/204.14 |
| 6,561,190 B1 | * | 5/2003 | Kwok ................... A61M 16/06 128/207.12 |
| 6,679,265 B2 | | 1/2004 | Strickland et al. |
| 7,255,107 B1 | | 8/2007 | Gomez |
| 7,341,059 B2 | | 3/2008 | Moody et al. |
| 7,406,966 B2 | | 8/2008 | Wondka |
| 7,493,902 B2 | | 2/2009 | White et al. |
| 7,559,327 B2 | | 7/2009 | Hernandez |
| 8,342,179 B2 | | 1/2013 | Hacke et al. |
| 8,844,530 B2 | | 9/2014 | Birnkrant |
| 9,032,955 B2 | | 5/2015 | Lubke et al. |
| 10,556,079 B2 | | 2/2020 | Tatkov |
| 11,185,653 B2 | | 11/2021 | O'Donnell et al. |
| 2002/0053347 A1 | | 5/2002 | Ziaee |
| 2002/0112730 A1 | | 8/2002 | Dutkiewicz |
| 2002/0122746 A1 | | 9/2002 | Yamamori et al. |
| 2003/0024533 A1 | | 2/2003 | Sniadach |
| 2003/0168063 A1 | | 9/2003 | Gambone et al. |
| 2004/0244799 A1 | | 12/2004 | Landis |
| 2004/0261797 A1 | | 12/2004 | White et al. |
| 2005/0011523 A1 | * | 1/2005 | Aylsworth ........ A61M 16/0069 128/207.18 |
| 2005/0028822 A1 | | 2/2005 | Sleeper et al. |
| 2005/0066976 A1 | | 3/2005 | Wondka |
| 2005/0098183 A1 | | 5/2005 | Nash |
| 2006/0081243 A1 | * | 4/2006 | McDonald .......... A61M 16/085 128/200.24 |
| 2006/0169281 A1 | * | 8/2006 | Aylsworth ........ A61M 16/0666 128/204.23 |
| 2006/0266361 A1 | | 11/2006 | Hernande |
| 2006/0278233 A1 | * | 12/2006 | McAuley ........... A61M 16/0066 128/206.12 |
| 2007/0079982 A1 | | 4/2007 | Laurent et al. |
| 2007/0089749 A1 | | 4/2007 | Ho et al. |
| 2007/0107737 A1 | | 5/2007 | Landis |
| 2007/0113848 A1 | | 5/2007 | Acker et al. |
| 2007/0113856 A1 | | 5/2007 | Acker et al. |
| 2007/0125380 A1 | | 6/2007 | Acker et al. |
| 2007/0125385 A1 | | 6/2007 | Ho et al. |
| 2007/0144518 A1 | | 6/2007 | Acker et al. |
| 2008/0060653 A1 | | 3/2008 | Hallett et al. |
| 2008/0078389 A1 | | 4/2008 | Xiao et al. |
| 2008/0276937 A1 | | 11/2008 | Davidson et al. |
| 2008/0295846 A1 | | 12/2008 | Han et al. |
| 2008/0319334 A1 | | 12/2008 | Yamamori |
| 2009/0000618 A1 | | 1/2009 | Warren |
| 2009/0101147 A1 | | 4/2009 | Landis et al. |
| 2009/0173349 A1 | | 7/2009 | Hernandez et al. |
| 2011/0009763 A1 | | 1/2011 | Levitzky et al. |
| 2011/0067704 A1 | | 3/2011 | Kooij et al. |
| 2012/0055480 A1 | | 3/2012 | Wilkinson |
| 2012/0125338 A1 | | 5/2012 | Yarahmadi |
| 2012/0167892 A1 | * | 7/2012 | Matula, Jr. .......... A61M 16/085 128/206.21 |
| 2012/0240935 A1 | | 9/2012 | Johansen |
| 2012/0285448 A1 | | 11/2012 | Dugan et al. |
| 2012/0305001 A1 | | 12/2012 | Tatkov |
| 2013/0213400 A1 | | 8/2013 | Barlow et al. |
| 2014/0096773 A1 | | 4/2014 | Amarasinghe |
| 2014/0107517 A1 | | 4/2014 | Hussain |
| 2014/0166015 A1 | | 6/2014 | Waggoner |
| 2014/0246025 A1 | | 9/2014 | Cragg et al. |
| 2015/0217074 A1 | | 8/2015 | Wells |
| 2016/0022948 A1 | | 1/2016 | Martin et al. |
| 2016/0082215 A1 | | 3/2016 | Bugamelli et al. |
| 2016/0282215 A1 | | 9/2016 | Naito et al. |
| 2016/0296720 A1 | | 10/2016 | Henry et al. |
| 2016/0339195 A1 | | 11/2016 | Raje et al. |
| 2017/0182275 A1 | | 1/2017 | O'Donnell et al. |
| 2017/0128689 A1 | | 5/2017 | Law et al. |
| 2020/0010250 A1 | | 1/2020 | Herling et al. |
| 2020/0101250 A1 | | 4/2020 | Nelson et al. |
| 2022/0096772 A1 | | 3/2022 | O'Donnell et al. |

FOREIGN PATENT DOCUMENTS

| | | |
|---|---|---|
| CN | 101237902 | 8/2008 |
| CN | 101365509 | 2/2009 |
| CN | 101489617 | 7/2009 |
| EP | 0747078 B1 | 10/2002 |
| EP | 1484075 | 12/2004 |
| EP | 1800707 | 6/2007 |
| EP | 1334742 B1 | 4/2008 |
| EP | 2515984 A1 | 10/2012 |
| EP | 3556418 | 10/2019 |
| JP | 2009-512510 | 3/2009 |
| JP | 2013-507205 A | 3/2013 |
| JP | 2013-515560 | 5/2013 |
| WO | WO 82/03548 | 10/1982 |
| WO | WO 2005/018524 | 3/2005 |
| WO | WO 2005/063328 | 7/2005 |
| WO | WO 2008/031149 | 3/2008 |
| WO | WO 2009/109005 | 9/2009 |
| WO | WO 2010/057166 | 5/2010 |
| WO | 2010/076704 A1 | 7/2010 |
| WO | 2011/030250 A1 | 3/2011 |
| WO | WO 2011/078702 | 6/2011 |
| WO | WO 2011/078703 | 6/2011 |

(56) References Cited

FOREIGN PATENT DOCUMENTS

| WO | 2012/154883 A2 | 11/2012 |
| WO | WO 2015/145390 | 3/2015 |
| WO | 2016/041019 A1 | 3/2016 |
| WO | 2016/201358 A1 | 12/2016 |
| WO | 2017/011864 A1 | 1/2017 |

OTHER PUBLICATIONS

EPO Supplementary Search Report for Application No. for PCT/NZ2010000260 dated Feb. 26, 2015, 5 pages.
SIPO Notification of First Office Action (PCT in National Phase) for Application No. 201080063516.0 dated May 6, 2014, 7 pages.
SIPO Second Office Action for Application No. 201080063516.0 dated Feb. 17, 2015, 4 pages.
International Search Report; PCT/NZ2010/000260; dated Apr. 27, 2011; 6 pages.
http://en.wikipedia.org/wiki/Oxygen_therapy. Viewed on Jan. 29, 2021.

* cited by examiner

BREATHING ASSISTANCE SYSTEM

FIELD OF THE INVENTION

The present invention relates to a respiratory user interface with improved dead space flushing.

BACKGROUND OF THE INVENTION

One method of treating respiratory distress and certain respiratory disorders (including Chronic Obstructive Pulmonary Disease or COPD and Obstructive Sleep Apnea or OSA) is the provision of Continuous Positive Airway Pressure (CPAP) or other forms of Positive Airway Pressure (PAP) to support a user's respiratory system. Non invasive respiratory pressurisation is commonly administered by delivering pressurised breathing gases to a user's mouth and/or nose.

PAP treatment is usually provided by a breathing assistance system. Breathing assistance systems generally incorporate a source of pressurised gases (potentially a compressor, pressurised gas canister or hospital compressed air supply) and an interface configured to deliver the pressurised gases to a user. Additionally, breathing assistance systems may incorporate a humidifier for heating and humidifying the breathing gases prior to delivery to the user.

Other supported breathing systems include ventilators and respirators. These may adjust pressure between inspiratory and expiratory phases of the breathing cycle, and typically include a return line from the interface.

Conventional interfaces are configured to form a seal with the user's face or upper airway to facilitate adequate pressurisation of the user's respiratory system. Forma™, Oracle™, Zest™ and Opus™ are examples of sealing respiratory user interfaces produced by Fisher & Paykel Healthcare. These interfaces are configured to seal with a user's face, mouth, nose and nares respectively.

The seal formed between the interface and user's respiratory system allows the mask pressure to be regulated by reducing gas leaks and providing a controlled breathing gases exhaust. Gases may be exhausted from the user interface directly to the surrounding atmosphere (through outlet vents) or to another component in the breathing assistance system responsible for controlling the exhaust of breathing gas.

Non-sealing interfaces, particularly nasal cannula, are often employed for supplemental oxygen therapy or other respiratory gases such as Heliox. Typical supplemental oxygen therapy interfaces deliver flow rates up to 5 l/min directly to the user's nares. Air from the user's surroundings is entrained with the oxygen during normal inhalation, the gases combining to deliver a gas mixture with elevated oxygen concentrations to the user's lungs.

Common supplemental oxygen therapy interfaces are supported by a pair of delivery lumen that loop over the user's ears. The lumen have small diameters (in the range 2-3 mm) and supply oxygen to both sides of the nasal cannula, providing essentially even flow to each nasal prong.

Facial masks are traditionally used for high flow oxygen therapy. Non-sealing high flow nasal cannula, such as Fisher & Paykel Healthcare's Optiflow™ Nasal Cannula, are also being promoted for flow rate based treatments (including high-flow oxygen therapy) where respiratory system pressure regulation is not a control objective.

Direct delivery of breathing gases to a user's nares can be advantageous as the gases can be administered at a greater temperature and humidity than is viable with facial masks.

In this specification, where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

An object of the present invention is to provide a user interface capable of delivering breathing gases to a user's nares and controlling expiratory pressure or to provide the industry or public with a useful choice.

In one aspect, the invention consists in a user interface comprising a non-sealing nasal cannula and a mask arranged about the nasal cannula, the mask including a seal configured to seal with a user's face to allow the interface to be pressurised, the cannula configured to deliver breathing gases to the nares of a user at a flow rate exceeding the intended user's peak inspiratory flow requirements so that the mask and the user's pharynx are flushed continuously with fresh breathing gases to reduce dead space.

According to a further aspect, the cannula includes one or a pair of nasal prongs, and the mask includes a gas outlet.

In a further aspect, the invention consists in a user interface comprising one or a pair of high flow non-sealing nasal prongs configured to deliver a flow of breathing gas to a user's nares, a mask arranged about the nasal prongs, a conduit connecting the prongs to an inlet outside the mask, a resilient sealing member configured to form a seal with a users face to allow pressurisation of the users respiratory system, and a gas outlet in the mask.

In a further aspect, the invention consists in a user interface comprising a nasal cannula, and a mask arranged about the nasal cannula, the nasal cannula comprising one or a pair of non-sealing nasal prongs configured to deliver a unidirectional flow of breathing gas in excess of an intended user's peak inspiratory flow requirements to the nares of a user and a conduit coupling the prongs to an inlet outside the mask, the mask comprising a resilient sealing member configured to form a seal with a user's face to allow pressurisation of the user's respiratory system, a gas supply passage through the mask between an inlet outside the mask and the nasal cannula, and a gas outlet passage through the mask configured to exhaust gases from the mask, the interface configured to deliver breathing gases exclusively through the nasal cannula and exhaust gases exclusively from the mask.

In a further aspect, the invention consists in a user interface comprising a nasal cannula including one or a pair of nasal prongs configured to deliver breathing gases to a user's nares, a mask arranged about the nasal cannula, a seal coupled to the mask and configured to seal with an intended user's face to allow the mask to be pressurised, a breathing gas inlet through the mask coupled to the nasal cannula, a gas outlet from the mask configured to exhaust expired gases, and headgear coupled to the mask to retain the interface in position on a user's head.

According to a further aspect, the prongs have a sufficient bore to supply a gas flow rate in excess of an intended user's peak inspiratory flow rate.

According to a further aspect, the user interface is configured to deliver breathing gases to an adult, and the prongs have an appropriate equivalent bore diameter to meet peak inspiratory flow requirements.

According to a further aspect, the user interface is configured to deliver breathing gases to an infant, and the prongs have an appropriate equivalent bore diameter to meet peak inspiratory flow requirements.

According to a further aspect, the gas outlet includes, or is configured to be coupled to, a variable pressure regulator.

According to a further aspect, the gas outlet is an adjustable restriction that exhausts gases to a user's surroundings.

According to a further aspect, the nasal prongs are configured to deliver breathing gas to a user's nares at a variable supply flow rate and the gas outlet is adjustable to regulate gas outlet pressure, the supply flow rate and mask pressure defining the end expiratory pressure experienced by the user.

According to a further aspect, the mask is shaped and sized to enclose a user's nose and mouth in use.

According to a further aspect, the user interface includes headgear configured to retain the user interface in position on the user's face.

According to a further aspect, the user interface includes a conduit connecting the nasal prongs to an inlet of the mask, wherein a distal end of the conduit is coupled to a connector part, the connector part is releasably engaged with a complimentary connector part coupled to the mask, the conduit and nasal prongs being detachable from the mask.

According to a further aspect, the prongs or the conduit include a coupling configured to receive headgear, allowing the prongs to be used independent of the mask.

According to a further aspect, the user interface includes a conduit connecting the nasal prongs to an inlet of the mask wherein the conduit supports the prongs within the mask and allows an angle of presentation of the prongs to be adjusted to suit an individual user's facial geometry.

According to a further aspect, the user interface includes a conduit connecting the nasal prongs to an inlet of the mask wherein the conduit supports the prongs within the mask and allows adjustment of the prongs in a depth direction corresponding to an anteroposterior direction of a user.

According to a further aspect, the user interface includes a conduit connecting the nasal prongs to an inlet of the mask wherein the conduit supports the prongs within the mask and allows adjustment of the prongs in a height direction corresponding to a superior-inferior direction of a user.

According to a further aspect, the user interface includes a conduit connecting the nasal prongs to an inlet of the mask wherein the conduit includes a malleable spine that extends from the connector to support the conduit and prongs, the spine configured to retain the conduit and prongs in a user set position.

According to a further aspect, the mask includes a hollow enclosure facing the wearer in use, the prongs are supported in the hollow enclosure by an adjustable support member.

According to a further aspect, the adjustable support member spans the hollow enclosure.

According to a further aspect, the adjustable support member is malleable.

According to a further aspect, the adjustable support member can adapt for adjustment in a depth direction corresponding to an anteroposterior direction of a user.

According to a further aspect, the adjustable support member can adapt for adjustment of the prongs in a height direction corresponding to a superior-inferior direction of a user.

According to a further aspect, the adjustable support member can adapt for adjustment of an angle of presentation of the prongs.

According to a further aspect, the gas outlet is an actively controlled PEEP valve that regulates the pressure within the mask to control end expiratory pressure.

According to a further aspect, at least a part of the mask, prongs or sealing member is formed of a breathable material.

According to a further aspect, the gas outlet is configured to couple with a conduit to transport exhausted gases to a pressure regulator for regulating mask pressure.

According to a further aspect, the sealing member is arranged about a peripheral edge adjacent an opening in the mask.

According to a further aspect, the user interface includes one or more additional injection ports for supplying gases to the mask cavity.

According to a further aspect, the conduit includes one or more outlets to the mask cavity, additional to the nasal prongs.

According to a further aspect, the mask is configured to receive a supply of gases to the mask cavity in addition to through the nasal prongs.

In a further aspect, the invention consists in a method of supplying breathing gas to a user comprising providing a high flow of heated and humidified breathing gases directly to the user's nares, providing a sealed pressurised space about the user's nose, and regulating the flow rate of gases supplied to the user's nares or the pressure within the mask to control the end expiratory pressure experienced by the user.

According to a further aspect, the breathing gases are provided at a temperature between 31° C. and 37.5° C. and humidity between 32 mg/L and 44 mg/L.

According to a further aspect, the breathing gases are provided in a substantially unidirectional flow.

In a further aspect, the invention consists in a nasal cannula comprising a pair of non-sealing nasal prongs configured to deliver a flow of breathing gases to a user's nares gases in excess of an intended user's peak inspiratory flow requirements, a short length of conduit coupled to the nasal prongs, a connector part coupled to a distal end of the conduit and configured to engage with a complimentary connector part within a respiratory mask to couple the cannula to an inlet outside the mask.

According to a further aspect, the nasal cannula further comprises a pair of cheek bearing portions extending laterally in opposing directions from a central portion of the cannula adjacent the prongs, each cheek bearing portions including a coupling adjacent a lateral edge, each coupling configured to engage with a complimentary coupling within a suitably adapted respiratory mask to locate the cannula.

According to a further aspect, the cheek bearing portions are fabricated from a soft pliable material to enable the cannula to be adjusted in an anteroposterior direction.

According to a further aspect, the conduit supports the prongs within the respiratory mask in use, the conduit allowing the cannula to be adjusted in a depth direction corresponding to an anteroposterior direction of a user According to a further aspect, the conduit supports the prongs within the respiratory mask in use, the conduit allowing the cannula to be adjusted in a depth direction corresponding to a superior-inferior direction of a user.

According to a further aspect, the conduit supports the prongs within the respiratory mask in use, the conduit allowing the angle of presentation of the prongs to be adjusted.

According to a further aspect, the conduit is less than 150 mm in length.

According to a further aspect, the nasal cannula further comprises a pair of cheek bearing portions extending laterally in opposing directions from a central portion of the cannula adjacent the prongs, the cheek bearing portions incorporating a malleable material configured to allocate an offset of the prongs from an intended user's face.

According to a further aspect, the conduit includes a malleable spine that extends between the connector and the prongs to support the cannula in position within the mask.

According to a further aspect, the nasal cannula further comprises a pair of cheek bearing portions extending laterally in opposing directions from a central portion of the cannula adjacent the prongs, each cheek bearing portion incorporating a malleable spine that allows the prongs to be located within a user's nares.

According to a further aspect, each cheek bearing portions including a coupling adjacent a lateral edge, each coupling configured to engage with a complimentary coupling within a suitably adapted respiratory mask to locate the cannula.

According to a further aspect, the conduit is less than 150 mm in length.

In a further aspect, the invention consist in a nasal cannula comprising a pair of non-sealing high flow nasal prongs, a short length of conduit coupled to the nasal prongs, and a connector part coupled to a distal end of the conduit and configured to engage with a complimentary connector part within a respiratory mask to couple the cannula to an inlet outside the mask, the conduit configured to support the prongs within the mask and facilitate adjustment of the cannula in anteroposterior and superior-inferior directions as well as an angle of presentation of the prongs within the mask in use.

According to a further aspect, the nasal cannula further comprises a pair of cheek bearing portions extending laterally in opposing directions from a central portion of the cannula adjacent the prongs, each cheek bearing portions including a coupling adjacent a lateral edge, each coupling configured to engage with a complimentary coupling within a suitably adapted respiratory mask to locate the cannula.

According to a further aspect, the cheek bearing portions are fabricated from a soft pliable material to enable the cannula to be adjusted in an anteroposterior direction.

According to a further aspect, the conduit supports the prongs within the respiratory mask in use, the conduit allowing the cannula to be adjusted in a depth direction corresponding to an anteroposterior direction of a user According to a further aspect, the conduit supports the prongs within the respiratory mask in use, the conduit allowing the cannula to be adjusted in a depth direction corresponding to a superior-inferior direction of a user.

According to a further aspect, the conduit supports the prongs within the respiratory mask in use, the conduit allowing the angle of presentation of the prongs to be adjusted.

According to a further aspect, the conduit is less than 150 mm in length.

According to a further aspect, the nasal cannula further comprises a pair of cheek bearing portions extending laterally in opposing directions from a central portion of the adjacent the prongs, the cheek bearing portions incorporating a malleable material configured to allocate an offset of the prongs from an intended user's face.

According to a further aspect, the conduit includes a malleable spine that extends between the connector and the prongs to support the cannula in position within the mask.

According to a further aspect, the nasal cannula further comprises a pair of cheek bearing portions extending laterally in opposing directions from a central portion of the cannula adjacent the prongs, each cheek bearing portion incorporating a malleable spine that allows the prongs to be located within a user's nares.

According to a further aspect, each cheek bearing portions including a coupling adjacent a lateral edge, each coupling configured to engage with a complimentary coupling within a suitably adapted respiratory mask to locate the cannula.

According to a further aspect, the conduit is less than 150 mm in length.

The term "comprising" as used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

This invention may also be said to consist broadly in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists of the foregoing and also envisages constructions of which the following gives examples only.

DETAILED DESCRIPTION

Figure 1:
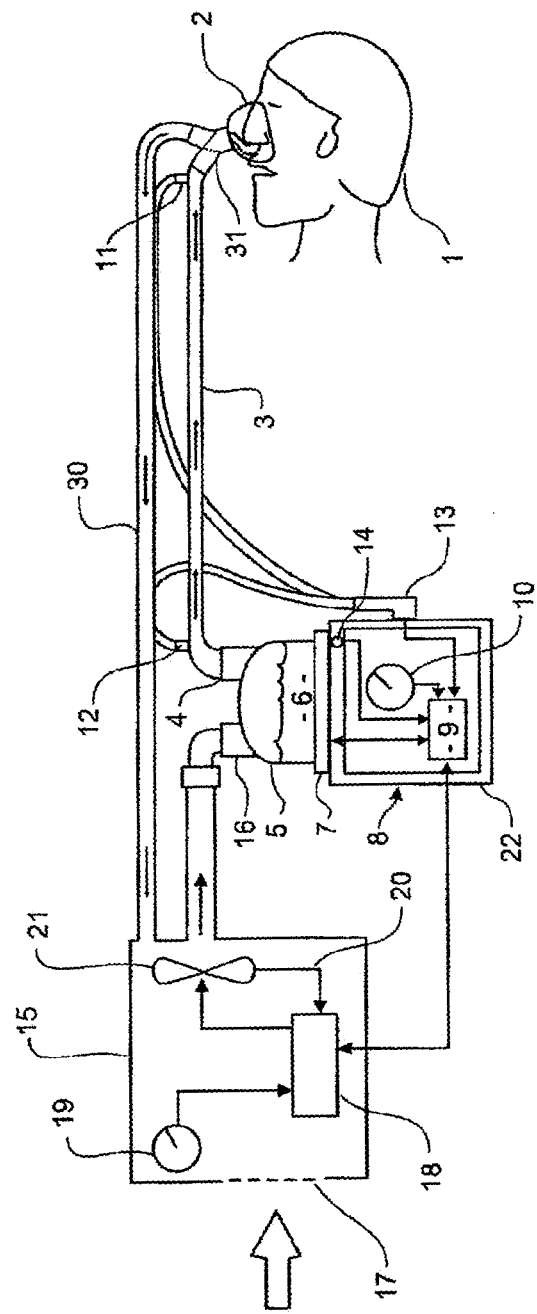
FIG. 1 is a schematic representation of a respiratory system configured to supply pressurised and humidified breathing gases to user through a nasal interface.

A breathing assistance system suitable for supplying breathing gases to user is illustrated in FIG. 1. The pictured breathing assistance system comprises a gas source 15, a separate humidifier 8, and a user interface 2.

The gas source 15 provides a supply of air to the humidifier 8. Ambient air is drawn into the gas source through an opening 17 in the gas source casing by an impeller 21. The rotational speed of the impeller 21 is modulated to regulate the quantity of air drawn into the gas source and the supply of breathing gases to the breathing assistance system.

The pressure and flow rate of gases exiting the gas source 15 is regulated by a controller 18. The controller manipulates the rotational speed of the impeller 21 and may incorporate feedback 20. A user control 19 may also be provided to allow the user to adjust the pressure or flow rate of gases exiting the gas source 15.

The illustrated gas source 15 represents an actively controlled flow generator similar to a hospital compressed air system or a ventilator or home CPAP unit (such as Icon™ or the SleepStyle™ series produced by the Fisher & Paykel Healthcare). Other gas sources, such as a compressed oxygen cylinder with suitable pressure or flow regulation, may also be used to supply breathing gases.

The outlet of the gas source 15 may be coupled to a separate humidifier unit 8. The humidifier unit 8 heats and humidifies the breathing gases prior to delivery to a user 1. In some apparatus, the humidifier may be integrated with the gas supply.

The humidifier 8 comprises a base unit 22 and a water chamber 5. The water chamber 5 is configured to hold water 6 and may be able to be disengaged from the humidifier base 22 to allow it to be filled or replaced. The humidifier 8 receives gases from the gas source 15 through water chamber inlet 16.

The humidifier base unit 22 includes a heater plate 7. The water chamber 5 rests on the heater plate 7 when engaged with the humidifier base 22. The heater plate 7 dissipates heat, generated by electrical resistance, to the water chamber 5. The water chamber 5 preferably has a heat conductive base to enable the heat generated by the heater plate 7 to pass efficiently to the water 6.

The water 6 is heated to form a vapour within the water chamber 5. The gases from the gas source 5 are heated and humidified by the vapour before exiting the water chamber 5 through gas outlet 4. A conduit 3 is coupled to the gas outlet 4. The conduit 3 transports gases from the humidifier 8 to the user interface 2.

The humidifier base unit 22 includes a controller 9 that regulates the temperature and humidity of the breathing gases. The controller 9 controls the supply of electrical energy to the heater plate 7.

The conduit 3 may incorporate a heater wire to heat the breathing gases during transportation to the user interface 2. The conduit heater wire is preferably receives power from the humidifier base unit 22.

Electrical contacts 11, 12 are provided at either end of the conduit 3. The contacts 11, 12 are coupled to the heater wire. A pair of transmission leads couple the respective contacts 11, 12 to a compatible coupling 13 in the humidifier base 22. The humidifier controller 9 regulates the power output from the humidifier base 22 to the heater wire to control the temperature of the breathing gases.

The controller 9 may receive feedback from various sensors incorporated in a control network throughout the breathing assistance system to monitor properties of the gases.

A heater plate temperature sensor 14 is provided adjacent the heater plate 7. Temperature, humidity, flow and other sensors may be provided within the conduit, adjacent the humidifier outlet 4 and the user interface 2. Power and signal transmission for sensors in the conduit may be provided through the conduit contacts 11, 12.

A user control 10 may also be provided as an input to controller 9. The user control 10 may allow a user to set properties of the gases, such as the temperature and humidity of gases being delivered through the user interface 2.

The gas source 15 may actively regulate the back pressure within the conduit 30 to control the end expiratory pressure experienced by the user 1. The expired gases may alternatively be exhausted to the user's surroundings through a fixed or adjustable restriction, or an actively controlled PEEP valve.

The conduit 3 distributes heated and humidified gases from the humidifier 9 to the user interface 2.

In some embodiments, an auxiliary conduit 30 may be provided to transport exhaust gases from the user interface 2 to the gas source 15. The supply conduit 3 and exhaust conduit 30 are coupled to the user interface 2 through a piece connector 31. The 'Y' piece connector 30 has separate inlets configured to couple to the respective conduits 3, 30 and concentric outlets that engage with the user interface 2.

The inner, outlet-port of the 'Y' piece connector couples the delivery conduit 3 to a nasal cannula within the mask. The outer port couples the exhaust conduit 30 to the mask to evacuate exhaust gases and excess breathing gases.

The user interface 2 couples the user 1 with the breathing assistance system, delivering heated and humidified gases from the humidifier 8 to the user's respiratory system. The illustrated user interface 2 comprises a nasal mask arranged about a nasal cannula. The nasal cannula is enclosed between the user's face and the mask.

The supply passage of the conduit 3 is coupled to the nasal cannula. Breathing gases are delivered from the humidifier 8 through the supply passage and nasal cannula to the nares of the user 1.

The exhaust passage of the conduit 30 is coupled to the 'Y' piece connector 31 which engages with an outlet in the mask. In other embodiments, the conduit 30 could be coupled directly to an outlet port of the mask.

In the illustrated embodiment, breathing gases are supplied exclusively through the nasal cannula and exhausted exclusively from the mask.

The cannula comprises a pair of prongs that project into the user's nares. The prongs preferably have a wide bore to permit high breathing gas flow rates (ideally, capable of delivering enough breathing gas for peak inspiratory demand with the lowest flow resistance), but do not seal with the user's nostrils.

It is preferable that flow through the cannula is continuous and unidirectional to constantly flush both mask and anatomical dead spaces of expired gases. Re-inhalation of expired $CO_2$ can be reduced by continuous purging of the user's nares with recently delivered breathing gases, forcing expired gases through the space about the nasal prongs. The expired gases are evacuated subsequently from the user interface 2 through an exhaust in the mask body.

Preferably, breathing gases are delivered at a flow rate exceeding the user's peak inspiratory flow requirements to ensure that expired gases are purged throughout the entire respiratory cycle.

Breathing gases delivered by the cannula may be administered exclusively to the user's nares, or a portion may be diverted into the mask (through outlets in the cannula base prior to the nares). An additional delivery inlet may be provided in the mask body to allow breathing gases to be delivered through both the mask and cannula.

Direct injection of correctly oriented breathing gases into the mask body adjacent the cannula may proffer the advantage of flushing expired gases away from the user's nostrils. Purging expired gases from about the user's nostrils provides an accessible source of supplemental breathing gases within the mask. This supplemental breathing gas source can augment the primary gas supplied to the nares when inspiratory flow requirements are not met.

The mask body is coupled to a peripheral seal that engages with the user's face. The seal prevents significant uncontrolled leaks between the user's face and the mask, enabling the pressure within the user's respiratory system to be regulated.

The delivery and exhaust of gases to and from the mask respectively may be controlled to regulate the pressure within the mask. Exhaust gas flow rates may be regulated actively by a component within the breathing assistance system (such as the gas supply device) or passively (by fixing the restriction to gas flow through variable or non-variable outlet vents). A combination of active and passive exhausting may be implemented alternatively.

In these ways, airway pressure experienced by a user can be regulated by manipulating the gas delivery flow rate supplied to the nasal cannula and the outlet flow rate exhausted from the mask A Positive End Expiratory Pressure (PEEP) can keep the airways and alveoli from collapsing at the end of expiration and also serve to reopen airways and alveoli that have already collapsed.

The therapeutic provision, PEEP, can improve gas exchange (by way of decreased intra pulmonary shunt), reduce the resistance to airflow (by reducing flow resistance within the lungs), and make the lungs less stiff (increased lung compliance). Levels of oxygen and carbon dioxide also may improve, reducing the need for supplemental oxygen and the sensation of breathlessness by the patient.

PEEP may also improve cardiac performance by increasing mean intra thoracic pressure. PEEP is of special advantage to assisting in the treatment of obstructive lung diseases and heart failure, including emphysema, bronchiectasis, chronic bronchitis, cystic fibrosis and pulmonary edema.

Additionally, breathing gases can be delivered to the user at, or near, optimal temperature and humidity (warmed and fully saturated with water vapour at body temperature −37° C., 44 mg/L humidity) as the gases are delivered predominantly to the user's nares. Subjects (patients) can tolerate greater gas temperatures and humidity when the gases are delivered to the nares than is viable when administered by facial mask.

Emulating the conditions within healthy adult lungs (37° C., 44 mg/L humidity) can help maintain healthy mucocilliary function in users with respiratory disorders affecting secretion.

The user interface 2 can therefore administer a broad range of treatments viably (including PAP and humidity therapy), as it combines the advantages of a sealing user interface (expiratory pressure regulation) and a high flow nasal interface (dead space flushing and optimal humidity delivery).

"Dead space" as used here refers to both apparatus dead space and anatomical dead space. Apparatus dead space refers to zones in any additional equipment such as mask and circuits where the expired gas can be re-breathed again. Anatomical dead space includes areas in the nose, pharynx, trachea and bronchi where $CO_2$ levels can build up. The high flow nasal interface can provide improved flushing of the anatomical dead space.

Several embodiments of interface are described in detail below. Each embodiment has aspects that suit particular delivery systems, however, these aspects could be easily used as alternatives in the other embodiments. For example, the nasal mask is described with features to provide a return path to the gas supply, but could alternatively have a vent to ambient surroundings (suitable for use with a flow generator lacking any gases return facility).

Nasal Cannula

Figure 7:
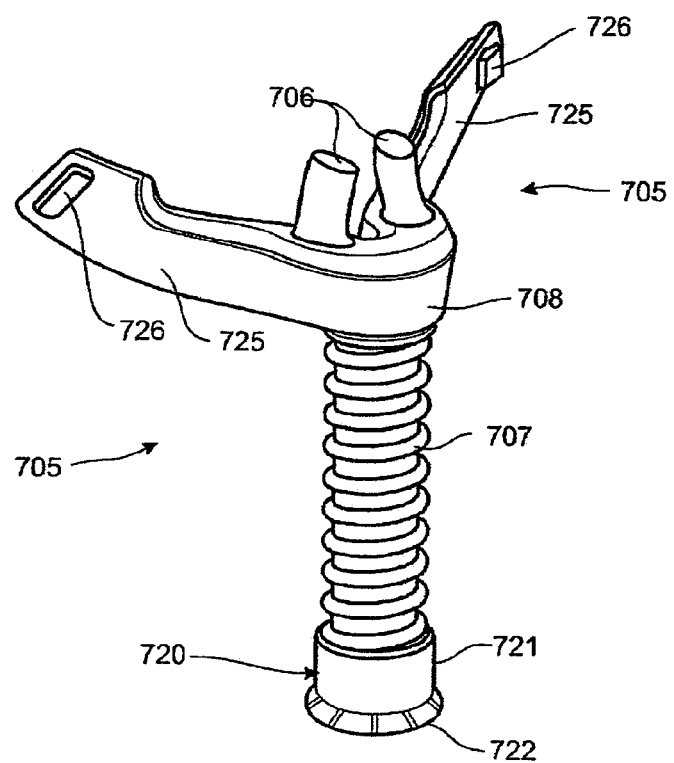
FIG. 7 is a three-dimensional representation of a non-sealing user interface, supply conduit, and connector suitable for use within a sealing respiratory mask.
Figure 8:
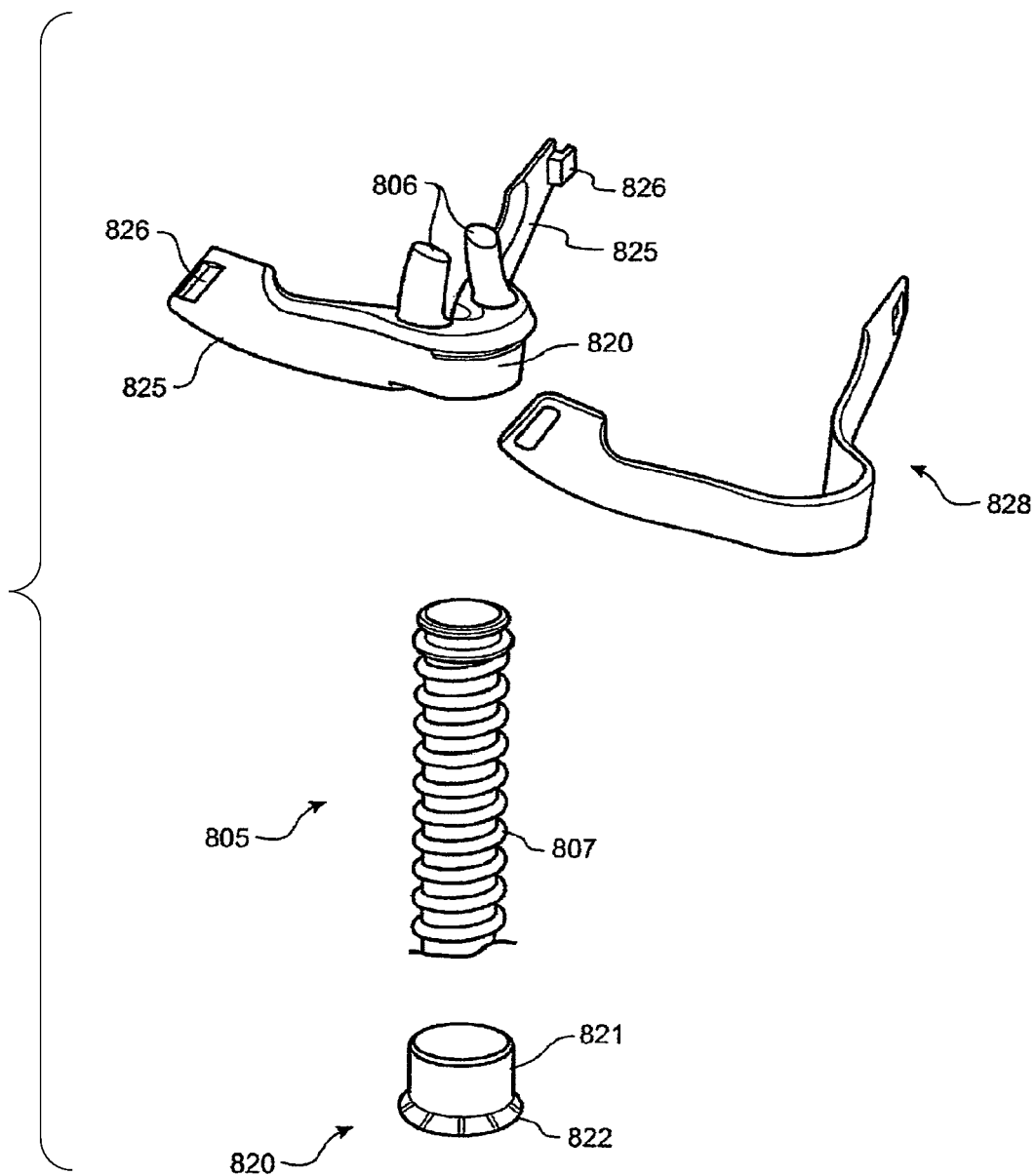
FIG. 8 is an exploded view of a non-sealing nasal interface, supply conduit, and connector suitable for use with a sealing respiratory mask.

An embodiment of a nasal cannula that can be combined with a suitable facial mask to form the desired hybrid interface is illustrated in FIGS. 7 and 8. The nasal cannula 705, 805, 905, 1005 comprises a pair of non-sealing nasal prongs 706, 806, 906, 1006 and a resilient supply conduit 707, 807.

The cannula 705, 805, 905, 1005 is arranged so that the conduit 707, 807 is oriented loosely along the superior-inferior axis in use. The nasal prongs 706, 806, 906, 1006 are coupled to a proximal end of supply conduit 707, 807. Each prong 706, 806, 906, 1006 is spaced approximately equidistant about the delivery conduit 707, 807 outlet. The separation between the prongs 706, 806, 906, 1006 generally correlates to the anticipated nasal septum width of the target user group (adult or infant) and the interface size (small, medium, large).

The prongs 706, 806, 906, 1006 extend outwardly from a distal base (coupled to the outlet of the conduit 707, 807) and terminate in a proximal delivery end situated away from the base. The proximal end of the illustrated nasal prongs 706, 806, 906, 1006 includes a delivery aperture. The delivery apertures convey breathing gases from the cannula to the respective nares of the user.

The delivery apertures may be aligned loosely, such that they are co-axial to the proximal end of the prong 706, 806, 906, 1006 as illustrated. Co-axial delivery apertures can cause jetting; the introduction of a coherent stream of breathing gases into the user's nares. Jetting results from the largely unchanged delivery path through the prong 706, 806, 906, 1006 and aperture (i.e. the prongs 706, 806, 906, 1006 act as nozzles directing the fluid stream). Delivery gas jetting can be advantageous for certain applications, including delivery noise reduction.

An alternative is for the nasal prongs to incorporate a cut-away delivery aperture to diffuse breathing gases introduced into the user's nares. The cut-away aperture is located preferably in a posterior face of the prong, so that a pocket of breathing gases is presented to the nasal cavities. The internal tip of the prong is curved preferably to provide a smooth flow path for gases exiting the cannula.

The cut-away configuration can reduce irritation of the nares by preventing high speed delivery of a concentrated breathing gas stream. The preferred configuration of a cannula incorporating cut-away nasal prongs is disclosed in Fisher & Paykel patent application Ser. No. 12/628,454, which is incorporated herein by reference.

The base of each prong 706, 806, 906, 1006 extends from a common inlet manifold 708, 808, 908. The manifold 708, 808, 908 couples the prongs 706, 806, 906, 1006 to the conduit 707, 807. The shape of the manifold 708, 808, 908 may be adapted to accommodate different prong 706, 806, 906, 1006 arrangements, including separations exceeding the conduit 707, 807 diameter (where the prong 706, 806, 906, 1006 base is positioned outside the circumference of the conduit 707, 807) as illustrated.

The nasal cannula may also incorporate a pair of cheek bearing portions 725, 825, 925, 1025. The cheek bearing portions 725, 825, 925, 1025 extend laterally outward from the manifold 708, 808, 908 and assist orientation of the prongs 706, 806, 906, 1006 in the user's nares. Preferably, the cheek bearing portions 725, 825, 925, 1025 are fabricated from the same silicone as the nasal prongs 706, 806, 906, 1006, or other suitably pliable and soft material.

The prongs 706, 806, 906, 1006 may curve from the base to the delivery end. Conventional nasal prongs incorporate a posterior curvature to follow the nasal cavity. Moderate posterior curvatures enable the prongs to fit comfortably within a wide range of nasal shapes.

Recent developments by Fisher & Paykel Healthcare have indicated that a neutral prong extension (no curvature from base to delivery end) or a mild anterior curvature may be advantageous in reducing interface noise. These developments, including preferred configurations of nasal cannula, are disclosed in U.S. patent application 61/262,297, which is incorporated herein by reference.

The nasal prongs 706, 806 are provided with a wide bore to minimise flow resistance and breathing gas entry velocity. The increased bore of the prongs 706, 806 enables a high flow of unidirectional breathing gases to be delivered to the user's nares in excess of an intended user's peak inspiratory flow requirements.

The expiration of respiratory gases by the patient against the high delivery flow may provide limited positive end expiratory pressure (PEEP). The amount of PEEP provided by non-sealing cannula generally varies between different users and is largely uncontrollable (as it is partly dependent on the exhalation exertion of the user).

Other factors that affect PEEP are the delivery flow rate, the fit of the cannula in the nares of a user (i.e. the allowance for expired gases to exit the nares) and the pressure drop across the supply line (including the main heated delivery tube, the unheated extension tube generally associated with the user interface, and the prongs).

The wide bore of the nasal prongs 706, 806 allows breathing gases to be delivered to the user in excess of peak inspiratory flow requirements. Exceeding the user's peak inspiratory flow requirements reduces re-inhalation of expired gases by providing continuous flushing of anatomical dead spaces (such as the pharynx) with fresh respiratory gases.

Additionally, a limited amount of positive pressure may be generated during the inspiratory phase. Inspiratory positive airway pressure (IPAP) keeps airways and alveoli from collapsing during inspiration, reducing the effort required to inhale. IPAP is of special advantage to patients who experience breathlessness as a result of respiratory failure.

The ability of the cannula to provide limited pressure support (Expiratory Positive Airway Pressure "EPAP" and IPAP) allows the cannula to administer pressure oscillations over the respiratory cycle. Pressure oscillations can improve the clearance of sputum from the lungs and the exchange of respiratory gases between the blood and alveolar air.

Another embodiment of nasal cannula that may be combined with a suitable respiratory mask is the Optiflow™ Nasal Cannula, produced by Fisher & Paykel Healthcare.

Nasal User Interface

Figure 2:
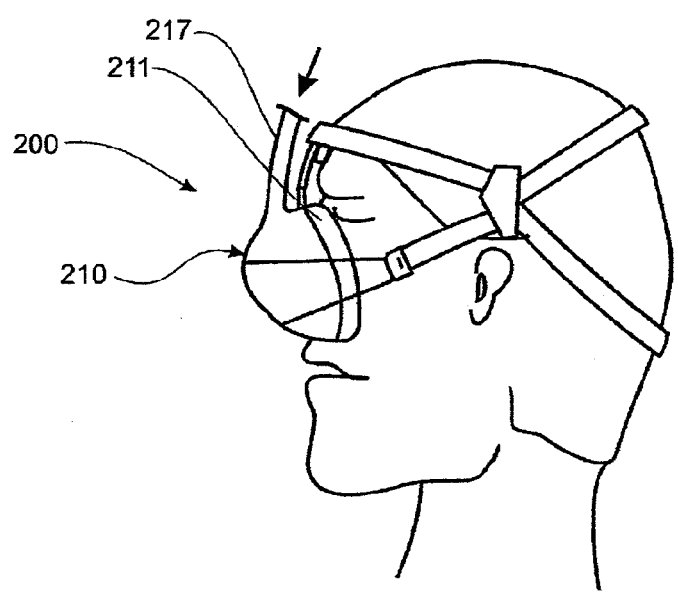
FIG. 2 is a schematic representation of a user with a nasal user interface retained in position by headgear coupled to the interface.
Figure 3:
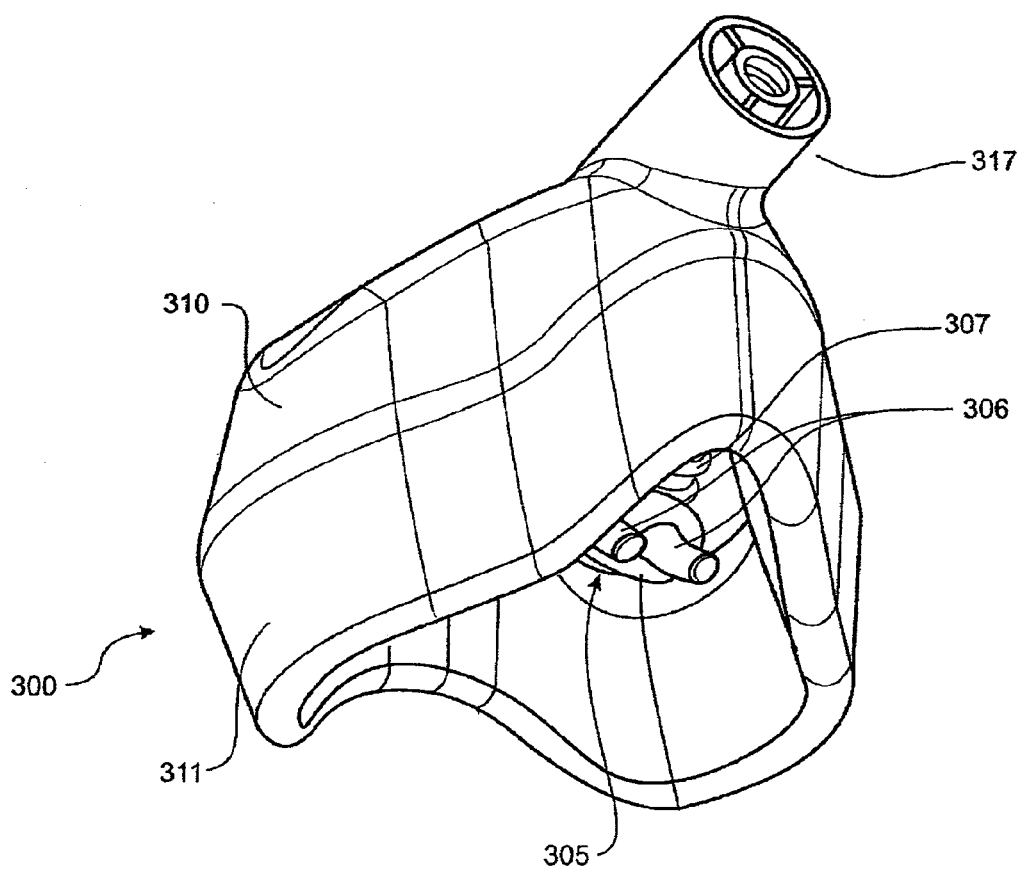
FIG. 3 is a three-dimensional representation of a nasal mask including a seal arranged about an outer periphery and a non-sealing nasal cannula positioned within the mask.

A user interface according to an embodiment of the present invention is illustrated in FIGS. 1-3. The interface 2, 200, 300 includes a facial mask that encloses the user's nose in use. The interface 2, 200, 300 comprises a mask body 210, 310 arranged about a nasal cannula 305. The cannula 305 is positioned within the mask body 210, 310 so that when the interface 2, 200, 300 is fitted to a user (as illustrated in FIGS. 1 and 2) the prongs reside within the user's nares.

The interface 200, 300 includes a mask conduit 217, 317. The mask conduit 217, 317 is configured to couple with a compatible breathing system conduit (such as designated number 3 in FIG. 1) to transfer breathing gases to and/or from the interface 2, 200, 300. Preferably, an extension of the mask conduit 217, 317 protrudes through the mask body 210, 310 to provide a coupling interface for the nasal cannula 305.

The mask conduit 217, 317 provides a configurable delivery pathway to the user interface 2, 200, 300 and is relatively short when compared with the breathing system conduit The mask conduit 217, 317 can have a fixed angular orientation (as illustrated in FIGS. 2 and 3) or may incorporate a swivel engagement with the mask body 210, 310. Angularly fixed conduits are commonly implemented with restrictive headgear (as illustrated in FIG. 2) to prevent movement of the mask conduit 217, 317 or breathing system conduit, that could disrupt the peripheral seal developed about the mask body 210, 310.

The mask conduit 217, 317 is coupled to the nasal cannula 305 to allow breathing gases to be delivered from an external gas source directly to the user's flares. It is preferable that the nasal cannula 305 incorporates a releasable coupling arranged on a distal end of the delivery conduit 307 and configured to engage with the mask body 210, 310.

An exemplary coupling is illustrated in FIGS. 7 and 8. The pictured coupling 720, 820 projects from the distal end of the conduit 707, 807 and is configured to engage with a portion of the mask conduit 217, 317 projecting internally.

The coupling 720, 820 comprises a base 721, 821, 921, 1021 that connects with the cannula conduit 707, 807, and a segmented annular wall 722, 822, 922, 1022. The segmented annular wall 722, 822, 922, 1022 extends away from the base 721, 821, 921, 1021 to a distal end of the coupling 720, 820.

The segments of the annular wall are arranged with a circumference, sized commensurately, with an extension of the mask conduit 217, 317 projecting internally (extending into the mask body 210, 310).

The internal extension of the mask conduit 217, 317 comprises a circumferential lip extending radially outward. The lip is positioned adjacent the projecting end of the mask conduit extension. The segmented annular wall 722, 822, 922, 1022 incorporates a complimentary, circumferential recess, positioned adjacent the distal end of the coupling 720 820, and oriented inwardly.

The coupling 720, 820 is aligned with, and forced over, the mask conduit extension to engage securely by interlocking with the circumferential recess and lip. The individual segments of the annular wall 722, 822, 922, 1022 splay outwardly during engagement and disengagement of the cannula 305 to accommodate the greater circumference of the lip.

It is preferable that the coupling allows the cannula 305 to swivel relative to the mask body 210, 310 (particularly, with a mask conduit incorporating angular adjustment) to prevent distortion of the cannula 305 from external twisting.

Figure 9:
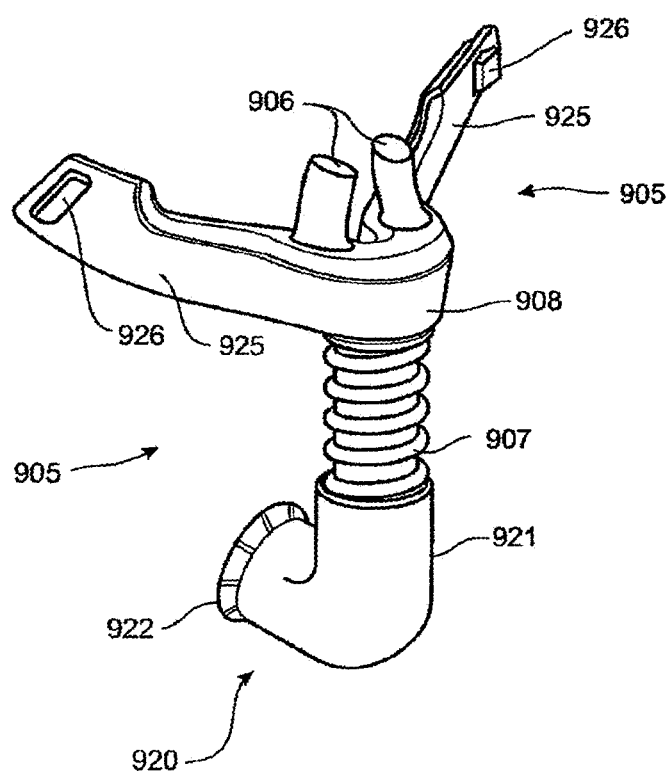
FIG. 9 is a three-dimensional representation of a non-sealing user interface, supply conduit, and elbow connector suitable for use within a sealing respiratory mask.
Figure 10:
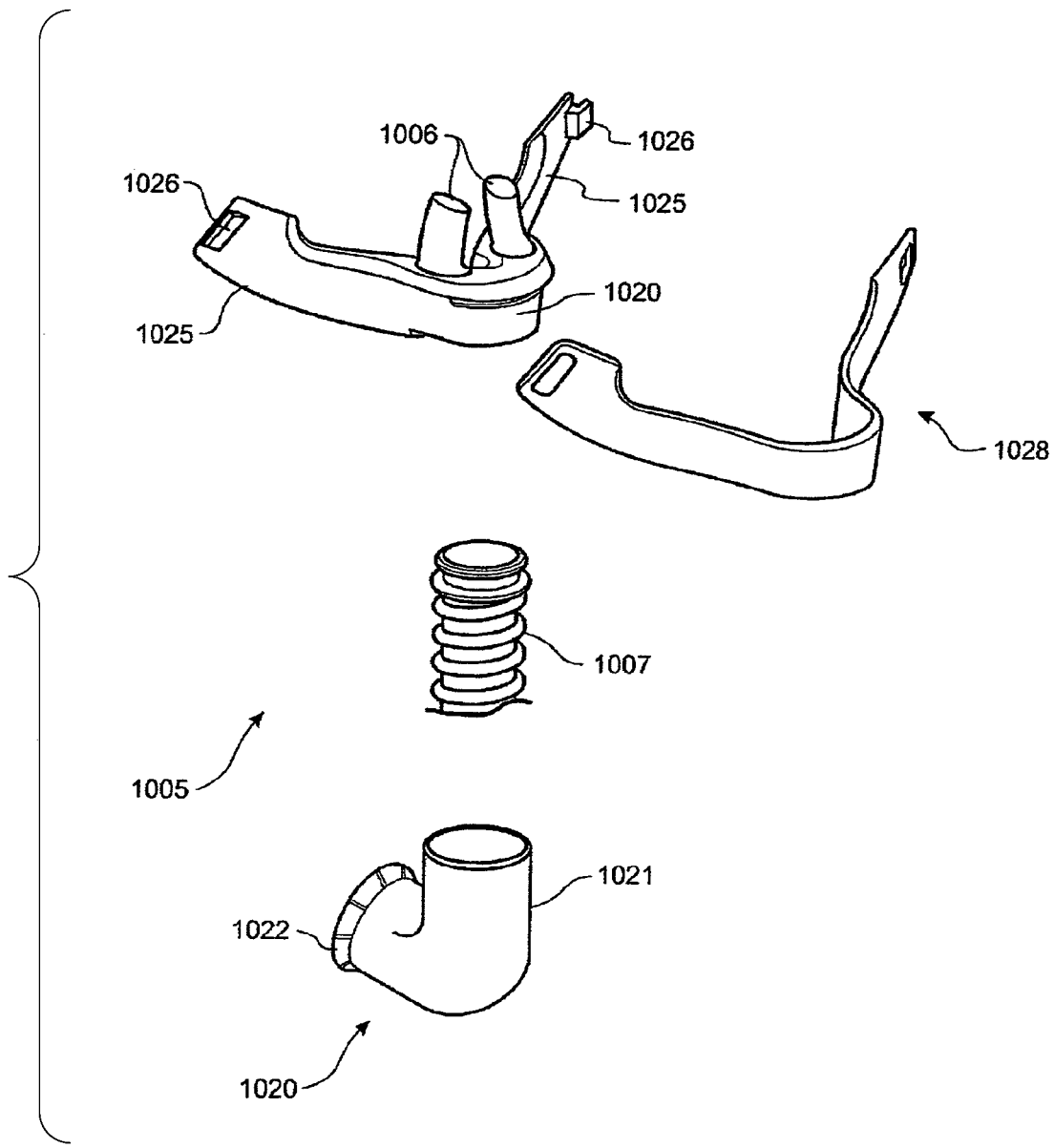
FIG. 10 is an exploded view of a non-sealing nasal interface, supply conduit, and elbow connector suitable for use with a sealing respiratory mask.

Another embodiment of connector is illustrated in FIGS. 9 and 10 with a comparable non-sealing nasal interface and conduit. The features of the non-sealing interface and conduit can be equated with the corresponding features (indicated by similar reference numbers) in FIGS. 7 and 8 respectively.

The connector 920, 1020, configured to couple the conduit 907, 1007 to a suitably adapted mask, incorporates an 'L' shaped bend. The elbow connector 920, 1020 orientates the cannula and promotes the prongs to a user in a suitable default configuration.

An auxiliary conduit (not shown) incorporating a suitable complimentary coupling may also be supplied with the interface 2, 200, 300 so that the cannula 305 can be used without the mask body 210, 310. It is anticipated that the cannula 305 can be employed independently during advanced stages of treatment to reduce the user's dependency on breathing assistance.

Couplings 726, 826, 926, 1026 are arranged adjacent the lateral edges of the cheek bearing portion 725, 825, 925, 1025 of the cannula 705, 805, 905, 1005 illustrated in FIGS. 7 and 8. The couplings 726, 826, 926, 1026 can engage with compatible headgear to support the cannula 305 when used independently of the mask. Preferably, the cheek bearing portions 725, 825, 925, 1025 are fabricated from a soft pliable material (such as silicone) to make the cannula 305 more comfortable. An additional rigid support 828, 1028 may be coupled to the anterior face of the manifold 708, 808 (and to cheek bearing portions 725, 825, 925, 1025 if they are present) to stabilize the cannula 705, 805, 905, 1005 and support the headgear.

The mask body 210, 310 may also be configured to receive the couplings 726, 826, 926, 1026 to locate and support the cannula 705, 805, 905, 1005 within the user interface, or the cannula 305 may be supported solely by the delivery conduit 307. The delivery conduit, 307, is preferably a ribbed polymer tube that is resilient and flexible so as to allow the cannula to 'float' within the mask body 210, 310.

The delivery conduit 307 may incorporate a malleable spine or insert to allow the position of the prongs to be allocated relative to the nares of the intended users. The spine may be fabricated with anisotropic stiffness (by selecting an appropriate shape or material) to bias the prongs toward a preferable orientation in order to minimise the amount of adjustment required.

Preferably, the spine connects with a rigid coupling at the base of the conduit 307. The rigid support provided by the coupling acts as an anchor for the spine, allowing the conduit and prongs can be adjusted relative to the base. The spine may extend the entire length of the conduit or a suitable portion of the conduit length to allow adequate adjustment.

Alternatively, the conduit may be fabricated from a sectioned tube that provides similar functionality to a malleable spine by allowing relative adjustment of the various sections.

Preferably, the cannula 305 support permits the angle of presentation of the prongs 306 to be adjusted in addition to translational adjustment loosely along the anteroposterior axis (depth), mediolateral axis (lateral), and superior-inferior axis (height).

In the system illustrated in FIG. 1, the gases expired by the user are exhausted from the user interface 2, 200, 300 through an expiratory limb. The illustrated expiratory limb is provided by conduit 30. The expiratory limb transports the expired gases from the user interface 2 to the ventilator. The humidifier may regulate the backpressure within the expiratory limb to control the pressure within the user interface 2. The pressure within the user interface 2 contributes to the expiratory pressure experienced by the user 1.

In alternate systems, the expired gases may vent directly from the mask to the surrounding. For example, variable restriction outlets (such as PEEP valves) and fixed outlet vents may be provided in the interface 2 to assist venting and expiratory pressure control. An outlet or vent on the mask could be a fixed or variable restriction. A variable restriction could be passively or actively controlled.

The pressure developed within the mask dominates PEEP generation, largely negating other factors that influence PEEP in non-sealing interfaces. As the pressure within the mask reflects the PEEP experienced by the user, controlling the mask pressure also controls PEEP. PEEP can therefore be regulated by active control of the exhaust gas flow rate from the mask.

Active control of mask pressure can be accomplished by use of an external pressure regulator (such as a suitably configured ventilator coupled to the interface by a return conduit) or an active PEEP valve in the mask body.

A suitable, actively controlled PEEP valve may be provided by a mechanical or electronic arrangement that regulates the pressure within the mask by controlling the exhaust flow rate or flow resistance.

The user interface 2, 200, 300 includes a seal 211, 311 to enable adequate pressures to be generated within the mask body 210, 310. The seal 211, 311 is arranged around an outer periphery of the mask body 210, 310 and is configured to contact the user's face and deform as necessary to adhere to the user's facial geometry.

The seal 211, 311 is formed preferably from a soft, pliable material such as foam, a suitable encapsulated gel (forming a gel pad), or silicone, to provide user comfort and functionality with low deformation forces. The seal 211, 311 may incorporate more than one material to improve the sealing capabilities and comfort of the mask.

A preferable configuration of seal incorporates an inner cushion, preferably formed of foam, and an outer sealing sheath, preferably formed of soft silicone, arranged about the cushion. The compliant outer sealing sheath contacts the user's face, deforming easily to form a primary seal. The cushion, although pliable, provides greater resistance to deformation.

The cushion and sheath deform independently of each other, allowing the cushion to provide a secondary seal by applying pressure to the sheath at a location separated from the primary seal. Greater disclosure of the preferred sealing arrangement is disclosed in Fisher & Paykel patent application Ser. No. 11/928,779, which is incorporated herein by reference.

Full Face User Interface

Figure 4:
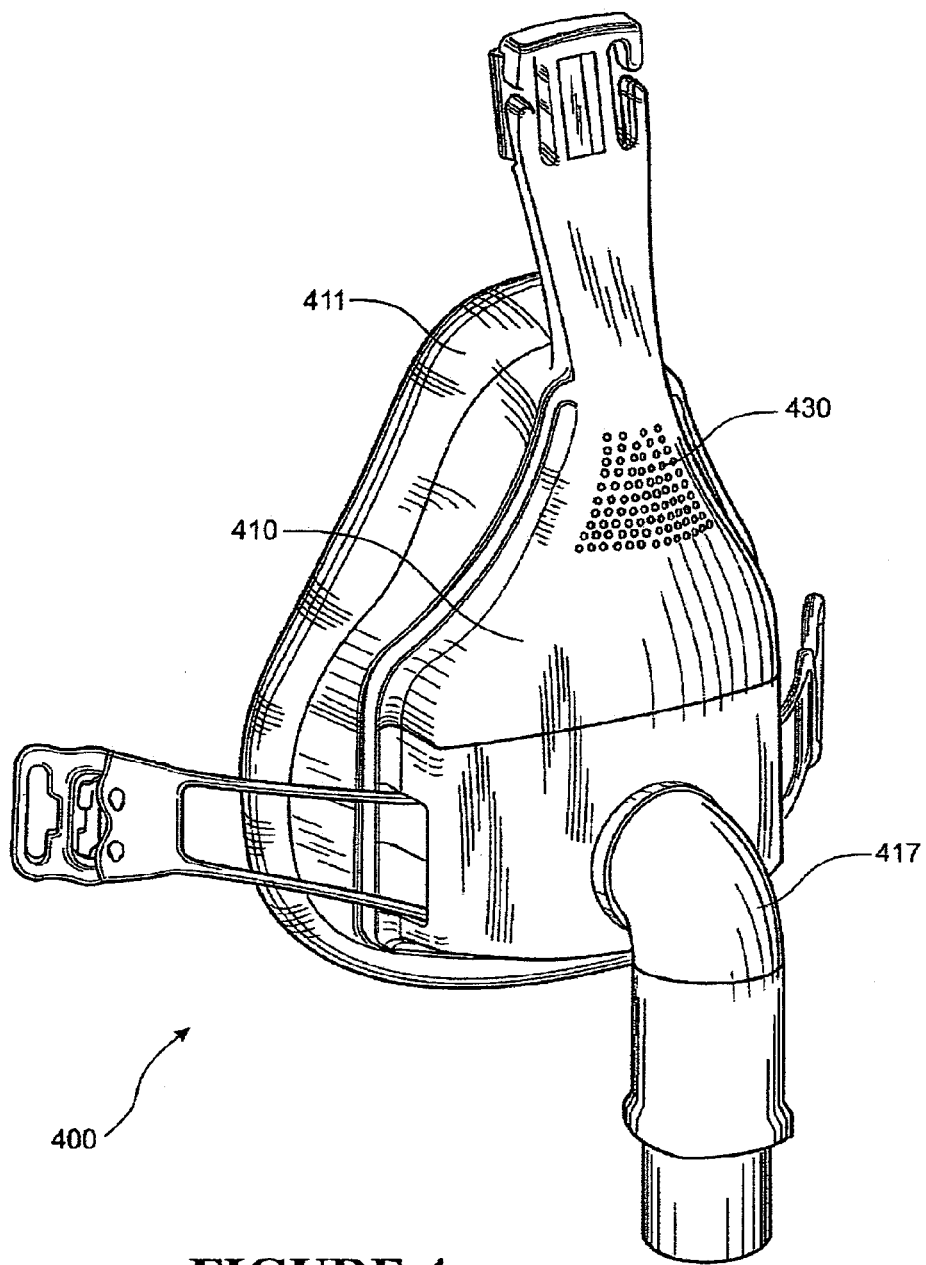
FIG. 4 is a three-dimensional representation of a full face user interface including a seal arranged around an outer periphery of the interface mask and ventilation holes in the mask shell.
Figure 5:
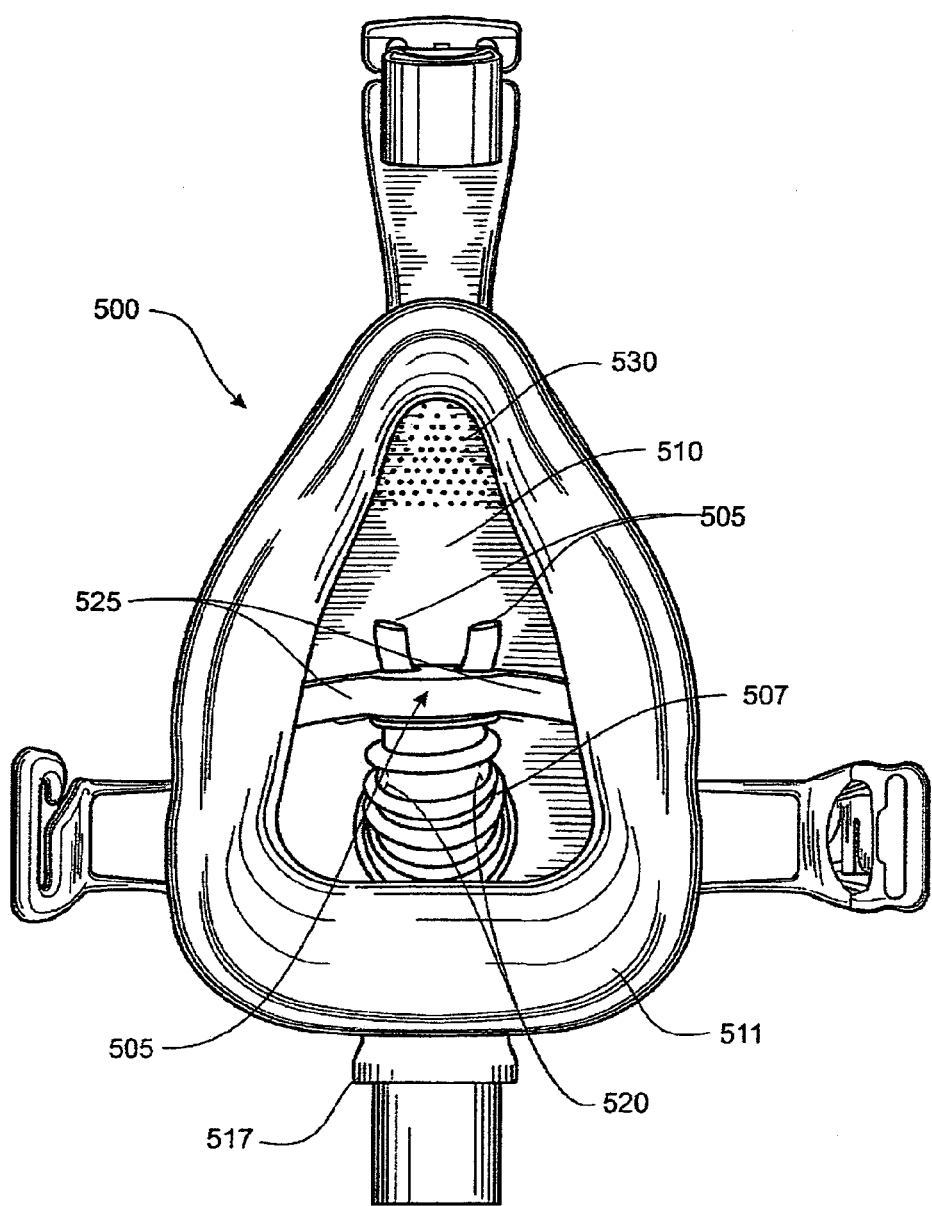
FIG. 5 is a rear view of a sealed full face user interface including a nasal cannula with a pair of non-sealing nasal prongs positioned within the mask and coupled to a gas inlet in the mask by an internal supply conduit.
Figure 6:
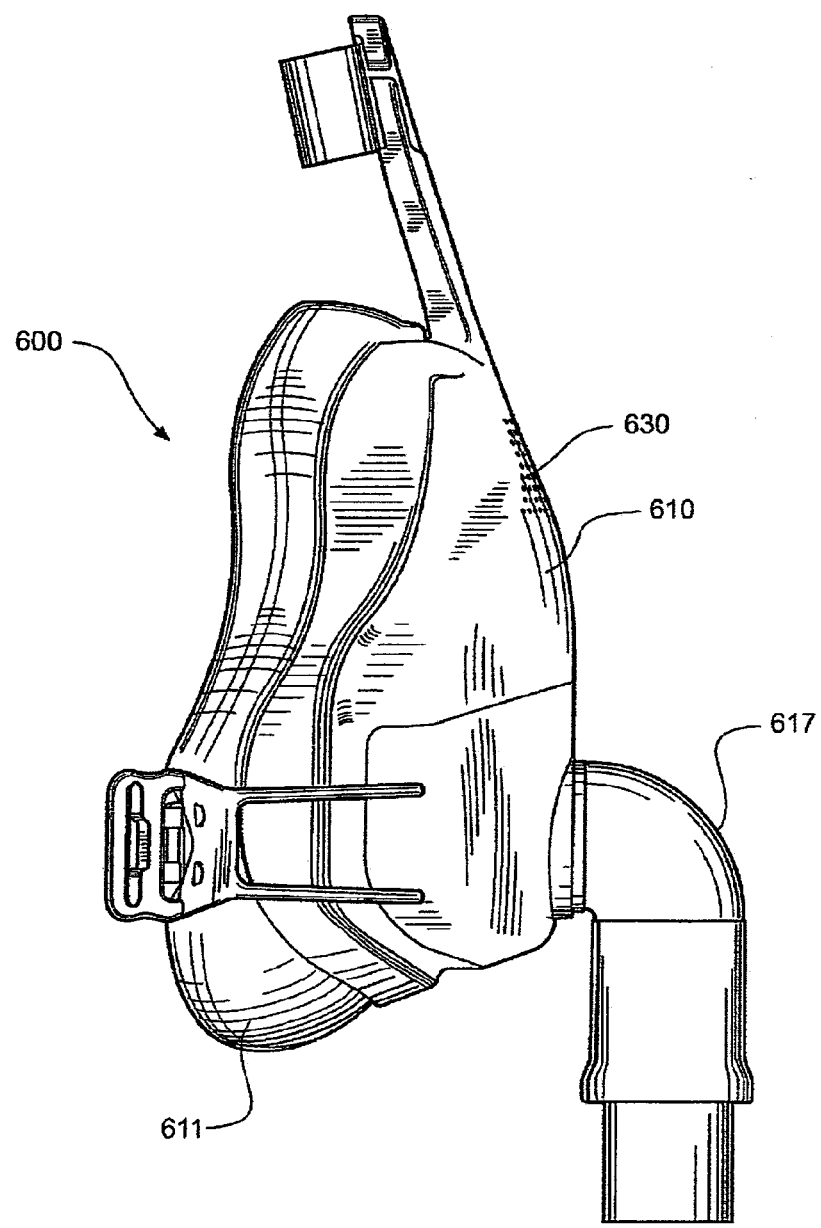
FIG. 6 is a side view of a full face mask including a seal arranged around an outer periphery of the mask body and ventilation holes.

A user interface according to another embodiment of present invention is illustrated in FIGS. 4-6. The interface 400, 500, 600 incorporates the features of the nasal interface 2, 200, 300, described previously, applied to a full face mask body 410, 510, 610. The mask body 410, 510, 610 encloses the user's mouth and nose in use.

The various combinations of alternate configurations described previously in relation to the nasal interface 2, 200, 300 are equally applicable to the full face interface 400, 500, 600. A number of minor variations illustrated in FIGS. 4-6 are described briefly in relation to the full face interface 400, 500, 600. These variations are also equally applicable to the nasal interface 2, 200, 300.

The user interface 400, 500, 600 incorporates a swivelling mask conduit 417, 517, 617 that permits the angle of the conduit 417, 517, 617 to be adjusted relative to the mask body 410, 510, 610.

The mask body 410, 510, 610 includes a plurality of venting apertures 430, 530, 630 positioned adjacent a nasal bridge section. The venting apertures 430, 530, 630 are responsible for exhausting expired gases from the user interface 400, 500, 600 directly to the user's surroundings.

The arrangement of the nasal cannula 505 within the mask body 510 is illustrated in FIG. 5.

The nasal cannula 505 may include cheek bearing portions 525 that extend laterally from a central portion of the cannula 505 adjacent the conduit 507.

The conduit 507 couples the cannula 505 to the mask inlet. In the pictured embodiment there is no provision for gases to exit the mask body 500 adjacent the conduit 507 base. However, an auxiliary exit may be provided in the interface 500, either co-axially about the conduit 507 or from another location in the mask body 510, to transport a portion of the expired gases to another breathing system component.

A variable restriction exhaust (such as a PEEP valve) may also be provided in the mask body 410, 510, 610 to accommodate variable venting directly to the user's surroundings. Variable restriction exhausts, can replace, or be provided in combination with, the fixed ventilation apertures 530. Preferably, some exhaust regulation is provided to assist regulation of pressure within the interface.

The user interface 400, 500, 600 includes a seal 411, 511, 611 arranged about a periphery of the mask body 410, 510, 610 to prevent significant leaks around the base of the interface 400, 500, 600 and enable adequate pressure to be developed within the mask.

The conduit 507 may include one or more outlets (illustrated in broken lines 520 in FIG. 5) to the mask cavity 510 to flush expired gases toward the venting apertures 530. Preferably, the venting apertures and breathing gas injection ports are positioned at opposed extremities of the mask cavity (as illustrated) to allow the injected gases to flush the entirety of the interface cavity.

The mask body 410, 510, 610 may incorporate sections of breathable material (such as SYMPATEX™ or NAFION™) in direct contact with both the mask cavity 410, 510, 610 and the surrounding environment. Suitable breathable materials allow the passage of water vapour from the mask cavity 410, 510, 610 to reduce condensation build up (often referred to as 'rain-out'). The ability to remove excess humidity from the mask body 410, 510, 610 is applicable particularly when the breathing gases are delivered at or near optimal humidity.

A preferred configuration of mask incorporating a breathable material is disclosed in Fisher & Paykel patent application Ser. No. 10/921,572, which is incorporated herein by reference. An alternate mask configuration involves integrating a foamed breathable material in the mask body 410, 510, 610.

Foaming can increase the permeability of such materials, allowing the mask to be fabricated from thicker sections without reducing the overall breathability. This is an area of active research for Fisher & Paykel Healthcare and subject of a co-pending United States patent application (yet to be assigned an application number) that is also incorporated herein by reference.

PREFERRED EMBODIMENTS OF THE INVENTION

Preferably, the prongs have a sufficient bore diameter to supply a gas flow rate in excess of an intended user's peak inspiratory flow rate.

Preferably, the user interface is configured to deliver breathing gases to an adult, the prongs having an appropriate equivalent bore diameter to meet peak inspiratory flow requirements.

Preferably, the user interface is configured to deliver breathing gases to an infant, the prongs having an appropriate equivalent bore diameter to meet peak inspiratory flow requirements.

Preferably, the gas outlet includes or is configured to be coupled to a variable pressure regulator.

Preferably, the gas outlet is an adjustable restriction that exhausts gases to a user's surroundings.

Preferably, the nasal prongs are configured to deliver breathing gas to a user's nares at a variable supply flow rate and the gas outlet is adjustable to regulate gas outlet pressure, the supply flow rate and mask pressure defining the end expiratory pressure experienced by the user.

Preferably, the mask is shaped and sized to enclose a user's nose and mouth in use.

Preferably, the user interface further includes headgear configured to retain the user interface in position on the user's face.

Preferably, a distal end of the conduit is coupled to a connector part, the connector part is releasable, and in use, is engaged with a complimentary connector part coupled to the mask, the conduit and nasal prongs being detachable from the mask.

Preferably, the prongs or the conduit include a coupling configured to receive headgear, allowing the prongs to be used independently of the mask.

Preferably, the conduit supports the prongs within the mask and allows an angle of presentation of the prongs to be adjusted to suit an individual user's facial geometry.

Preferably, the conduit supports the prongs within the mask and allows adjustment of the prongs in a depth direction corresponding to an anteroposterior direction of a user.

Preferably, the conduit supports the prongs within the mask and allows adjustment of the prongs in a height direction corresponding to a superior-inferior direction of a user.

Preferably, the conduit includes a malleable spine that extends from the connector to support the conduit and prongs, the spine configured to retain the conduit and prongs in a user set position.

Preferably, the mask includes a hollow enclosure, oriented towards the wearer in use, and the prongs are supported in the hollow enclosure by an adjustable support member.

Preferably, the adjustable support member spans the hollow enclosure.

Preferably, the adjustable support member is malleable.

Preferably, the adjustable support member can adapt for adjustment in a depth direction corresponding to an anteroposterior direction of a user.

Preferably, the adjustable support member can adapt for adjustment of prongs in a height direction corresponding to a superior-inferior direction of a user.

Preferably, the adjustable support member can adapt for adjustment of an angle of presentation of the prongs.

Preferably, the gas outlet is an actively controller PEEP valve that regulates the pressure within the mask to control the end expiratory pressure experienced by a user.

Preferably, at least a part of the mask, cannula or sealing member being formed of a breathable material.

Preferably, the sealing member is arranged about a peripheral edge adjacent an opening in the mask.

Preferably, the nasal cannula further comprises a pair of cheek bearing portions extending laterally in opposing directions from a central portion of the cannula adjacent the prongs, each cheek bearing portion including a coupling adjacent a lateral edge, each coupling configured to engage with a complimentary coupling within a suitably adapted respiratory mask to locate the cannula.

Preferably, the cheek bearing portions are fabricated from a soft pliable material to enable the cannula to be adjusted in an anteroposterior direction.

Preferably, the conduit supports the prongs within the respiratory mask in use, the conduit allowing the cannula to be adjusted in a depth direction corresponding to an anteroposterior direction of a user.

Preferably, the conduit supports the prongs within the respiratory mask in use, the conduit allowing the cannula to be adjusted in a depth direction corresponding to a superior-inferior direction of a user.

Preferably, the conduit supports the prongs within the respiratory mask in use, the conduit allowing the angle of presentation of the prongs to be adjusted.

Preferably, the conduit is less than 150 mm in length.

Preferably, the nasal cannula further comprises a pair of cheek bearing portions extending laterally in opposing directions from a central portion of the cannula adjacent the prongs, the cheek bearing portions incorporating a malleable material configured to allocate an offset of the prongs from an intended user's face.

Preferably, the conduit includes a malleable spine that extends between the connector and the prongs to support the cannula in position within the mask.

Preferably, the nasal cannula further comprises a pair of cheek bearing portions extending laterally in opposing directions from a central portion of the cannula adjacent the prongs, each cheek bearing portion incorporating a malleable spine that allows the prongs to be located within a user's nares.

Preferably, each cheek bearing portions including a coupling adjacent a lateral edge, each coupling configured to engage with a complimentary coupling within a suitably adapted respiratory mask to locate the cannula.

Preferably, the conduit is less than 150 mm in length.

Preferably, the breathing gases are provided at a temperature between 31° C. and 37.5° C. and absolute humidity between 32 mg/L and 44 mg/L.

Preferably, the breathing gases are provided in a substantially unidirectional flow.

The invention claimed is:

1. A user interface comprising:
a mask having a mask body and a seal coupled to the mask body, the seal configured to seal with a user's face to allow a cavity defined by the mask body to be pressurized and provide positive airway pressure support during inhalation and exhalation;
a nasal cannula including a pair of nasal prongs configured to deliver breathing gases to a user's respective nares, the nasal cannula extending into the mask cavity;
headgear coupled to the mask to retain the user interface in position on a user's head;
the mask body comprising a single breathing gas inlet, the single breathing gas inlet configured to be coupled with a single conduit to allow breathing gases to be delivered to both the cavity of the mask and the nasal cannula; and
a gas outlet from the mask body configured to exhaust expired gases;
wherein, upstream from the pair of nasal prongs relative to the flow of breathing gases entering the mask from the single breathing gas inlet, the breathing gases are allowed to flow into the mask cavity,
wherein the user interface is configured to receive the breathing gases from the single conduit.

2. The user interface of claim 1, further comprising a coupling between the nasal cannula and the mask body.

3. The user interface of claim 2, wherein the coupling comprises a base and a segmented annular wall extending away from the base.

4. The user interface of claim 1, wherein the nasal cannula comprises a conduit extending between and connecting the breathing gas inlet and the pair of nasal prongs.

5. The user interface of claim 4, further comprising a manifold coupling the conduit and the pair of nasal prongs.

6. The user interface of claim 4, further comprising a segmented annular wall extending radially outward of the conduit.

7. The user interface of claim 1, wherein the gas outlet is a fixed restriction that is adapted to be used to exhaust gases to a user's surroundings.

8. The user interface of claim 1, wherein the mask is shaped and sized to enclose a user's nose and mouth in use.

9. The user interface of claim 1, wherein the mask is shaped and sized to enclose a user's nose in use.

10. The user interface of claim 1, wherein the gas outlet consists of a plurality of venting apertures for exhausting expired gases from the user interface directly to the user's surrounding.

11. A user interface comprising:
a mask having a mask body and a seal coupled to the mask body, the seal configured to seal with a user's face to allow a cavity defined by the mask body to be pressurized and deliver breathing gases to the user's mouth and nose;
a pair of nasal prongs configured to deliver breathing gases to a user's nares;
a wall extending laterally across the cavity of the mask body, the wall dividing an upper portion of the mask body from a lower portion of the mask body, the the pair of nasal prongs extending from the wall;
a gas outlet in the upper portion of the mask body, the gas outlet consisting of a plurality of venting apertures for exhausting expired gases directly to the user's surroundings;
a single breathing gas inlet in the lower portion of the mask body, the single breathing gas inlet configured to be coupled with a single conduit to allow breathing gases to be delivered orally and nasally, wherein the user interface is configured to receive the breathing gases from the single conduit;
wherein, upstream from the pair of nasal prongs relative to the flow of breathing gases entering the mask from the single breathing gas inlet, the breathing gases are allowed to flow into the mask cavity; and
headgear coupled to the mask to retain the user interface in position on a user's head.

12. The user interface of claim 11, further comprising a coupling between the pair of nasal prongs and the mask body.

13. The user interface of claim 12, wherein the coupling comprises a base and a segmented annular wall extending away from the base.

14. The user interface of claim 11, further comprising a conduit extending between and connecting the single breathing gas inlet and the pair of nasal prongs.

15. The user interface of claim 14, further comprising a manifold coupling the conduit and the pair of nasal prongs.

16. The user interface of claim 14, further comprising a segmented annular wall extending radially outward of the conduit.

17. The user interface of claim 11, wherein the gas outlet is a fixed restriction that is adapted to be used to exhaust gases to a user's surroundings.

* * * * *

UNITED STATES PATENT AND TRADEMARK OFFICE
CERTIFICATE OF CORRECTION

PATENT NO. : 12,023,443 B2
APPLICATION NO. : 16/528159
DATED : July 2, 2024
INVENTOR(S) : Stanislav Tatkov It is certified that error appears in the above-identified patent and that said Letters Patent is hereby corrected as shown below:

In the Specification

Column 5, Line 59, after "the" insert -- cannula --.

Column 8, Line 19, after "a" insert -- 'Y' --.

Column 9, Line 25, delete "mask" and insert -- mask. --.

Column 12, Line 11 (approx.), delete "conduit" and insert -- conduit. --.

Column 12, Line 23, delete "flares." and insert -- nares. --.

In the Claims

Column 18, Line 36, Claim 11, delete "the the" and insert -- the --.

Signed and Sealed this
Seventeenth Day of September, 2024

Katherine Kelly Vidal
*Director of the United States Patent and Trademark Office*